United States Patent [19]
Wilson

[11] Patent Number: 5,942,675
[45] Date of Patent: Aug. 24, 1999

[54] OVEN CAVITY INSERT IN AN ANALYTICAL INSTRUMENT

[75] Inventor: William H. Wilson, Newark, Del.

[73] Assignee: Hewlett-Packard Company, Palo Alto, Calif.

[21] Appl. No.: 09/027,578

[22] Filed: Feb. 23, 1998

[51] Int. Cl.⁶ .................................................. G01N 30/00
[52] U.S. Cl. ............................ 73/23.35; 73/23.4; 95/82; 94/101
[58] Field of Search .................................. 73/23.35, 23.4, 73/865.6; 95/82; 96/101, 102; 432/166, 167

[56] References Cited

U.S. PATENT DOCUMENTS

| | | |
|---|---|---|
| 5,195,384 | 3/1993 | Duesler, Jr. et al. .................. 73/865.6 |
| 5,637,812 | 6/1997 | Baker et al. ............................ 73/865.6 |

Primary Examiner—Daniel S. Larkin
Attorney, Agent, or Firm—Mark Z. Dudley

[57] ABSTRACT

Energy efficiency of a thermal zone in an analytical instrument is improved by use of an oven cavity insert that may be removably positioned in an insulated enclosure in an oven cavity housing, whereby the combination of the oven cavity insert and one or more of the enclosure walls completely encloses a first space suitable for effecting the thermal zone. The oven cavity insert is positionable so as to separate the first space from at least a portion of the unused volume of the oven cavity, thus reducing the volume of the thermal zone, so as to reduce the amount of heating or cooling required for temperature control of a component positioned therein. When present in the oven cavity, the contemplated oven cavity insert effectively conceals a portion of the housing from the thermal zone, thus reducing the effective thermal mass of the oven cavity housing.

26 Claims, 9 Drawing Sheets

OVEN CAVITY INSERT IN AN ANALYTICAL INSTRUMENT

FIELD OF THE INVENTION

The present invention relates to methods and apparatus for the provision of a controlled thermal environment, and, more particularly, for an oven cavity insert suitable for improving the thermal control of a component positioned in a thermal zone in an analytical instrument.

BACKGROUND OF THE INVENTION

Modern analytical instruments are particularly susceptible to performance variations due to the thermal sensitivity of certain components that operate within the analytical instrument. The temperature of one or more components of an analytical instrument is typically controlled by locating the component in a temperature-controlled environment, or thermal zone. The temperature of the thermal zone is typically, effected by an electrically-powered heating device or cooling device, or a combination of such devices.

One particular type of analytical instrument is a chromatograph. The basic components of a chromatograph include an injection port for introducing a sample of matter to be examined into a stream of carrier fluid, a separation column attached to the injection port that causes some of the constituents of the sample to elute at different times, and a detector for producing a signal indicative of the presence of the constituents being eluted. A signal processing section may be employed for integrating the signal so as to provide information as to the quantity of each constituent.

In the typical gas chromatograph, the temperature controlled zone is constructed as an oven. The injection port and detector are attached to respective pneumatic fittings on the oven housing, and the separation column, usually mounted on a basket, is attached between the pneumatic fittings and located within the oven. The oven housing typically comprises a door and an enclosure having several insulated oven housing walls. A heating element and a stirring fan located in the oven respectively heats and stirs the air contained within the oven housing so as to minimize temperature gradients therein that could adversely affect the performance of the chemical process occurring within the column. During a typical sample analysis, the heating element is operated so as to increase the temperature of the oven from a minimum initial value to a maximum final value. Before introduction of the next sample into the column, the temperature of the oven is usually returned to its initial value.

Accordingly, with repeated cycling of the heating unit, fan, and other such devices, a large amount of energy is generated and dissipated, and thus the chromatograph consumes a considerable amount of power.

Further, the chromatograph is sometimes constructed for simultaneous operation of more than one column located within the thermal zone. With additional columns, detectors, injectors, and related devices, this construction allows such a chromatograph to operate in a wide variety of different configurations and methods for sample analysis. However, a large oven cavity is required to accommodate the increased number of components. When the oven is operated with but one injector, column, and detector, a large proportion of the oven cavity is unoccupied and is unused. Nevertheless, the entire oven cavity is subject to the usual patterns of heating and cooling. The temperature control system also exhibits an oven temperature ramp rate that is less than desirable, i.e., the time required for heating and cooling the oven cavity is too long. The overall efficiency of the oven is, therefore, sub-optimal.

Accordingly, the conventional chromatograph is best suited for use in the laboratory, or similar settings, where sufficient space and electrical power are available. There have been attempts to reduce the size and complexity of a chromatograph so as to be practical outside of the laboratory. Such miniaturization has not been fully realized, due in part to the power demands put on the system by an inefficient oven, and due to the large size and large thermal mass that is presented by the typical oven housing.

There is, accordingly, an unresolved need for a compact, reliable, and efficient system for providing the requisite control of a thermal zone in an analytical instrument.

SUMMARY OF THE INVENTION

I have determined that the energy efficiency of a thermal zone in an analytical instrument is improved by use of an oven cavity insert that may be removably positioned in an insulated enclosure in an oven cavity housing, whereby the combination of the oven cavity insert and one or more of the enclosure walls completely encloses a first space suitable for effecting the thermal zone. The oven cavity insert is positionable so as to separate the first space from at least a portion of the unused volume of the oven cavity, thus reducing the volume of the thermal zone, so as to reduce the amount of heating or cooling required for temperature control of a component positioned therein. When present in the oven cavity, the contemplated oven cavity insert effectively conceals a portion of the housing from the thermal zone, thus reducing the effective thermal mass of the oven cavity housing. Temperature control of the thermal zone may be accomplished faster and more efficiently than found in the prior art.

In the preferred embodiment of the invention, the oven cavity insert includes a body positionable within the oven cavity, wherein the body exhibits a size and shape sufficient to fit transversely within the enclosure so as to divide the oven cavity into a first space defining a thermal zone and a second space that is constituted by the remainder of the oven cavity and which is set apart from the thermal zone. The body includes a working surface which faces the thermal zone. The oven cavity insert impedes heat transfer between the first and second spaces. The thermal zone may thus be subject to temperature control without requiring similar temperature control of the second space.

In another embodiment of the invention, the oven cavity insert includes a body having a working surface formed of insulating material so as to impede heat transfer between the first space and the second space.

In another embodiment of the invention, the oven cavity insert includes a body having a working surface formed of heat-reflecting material so as to impede heat transfer between the first space and the second space.

In another embodiment of the invention, the oven cavity insert includes a body formed of insulating material so as to impede heat transfer between the first space and the second space.

In another embodiment of the invention, the working surface of the oven cavity insert is shaped so as to conform to a thermal envelope about the component, whereby the envelope corresponds to the volume occupied by the component located in the thermal zone and includes a marginal volume disposed about the component so as to permit air flow around the component for efficient temperature control of the component.

In another preferred embodiment of the invention, the component is provided in the form of a coiled separation column located at a central portion of the first space, and wherein the working surface of the oven cavity insert is shaped to include a central protrusion which extends into the central portion of the first space, whereby airflow about the separation column is circulated between the perimeter of the first space and the central portion of the first space.

In another preferred embodiment of the invention, the working surface of the oven cavity insert is shaped to include one or more surface features, whereby air flow about the component is directed to flow between the perimeter of the first space and the central portion of the first space, and wherein efficient circulation of air flow through the thermal zone is effected and eddy currents in the air flow are avoided. Contemplated surface features include a spiral arrangement of recesses, fins, vanes, or the like that are configured to facilitate a vortex pattern of air flow over the working surface of the oven cavity insert.

In another preferred embodiment of the invention, the outer edge of the working surface is configured to merge with the enclosure in a smooth transition, whereby air flow about the component is directed to flow between the perimeter of the first space and the central portion of the first space, and wherein efficient circulation of air flow through the thermal zone is effected and eddy currents in the air flow are minimized.

The advantages of the invention may be realized in a preferred embodiment of a chromatographic assembly suitable for use with a control system so as to provide an analytical instrument. The chromatographic assembly includes a housing having an insulating enclosure for confining an oven cavity defined therein, a temperature control assembly for establishing a thermal zone in the oven cavity, an injector section, a detector section, and a separation column located within temperature-controlled zone and having inlet and outlet ends attached to the injector section and detector section. The housing includes a door mounted on a door opening in the enclosure which allows access to the temperature-controlled zone. An oven cavity insert is positionable within the oven cavity, wherein the insert exhibits a size and shape sufficient to fit transversely within the enclosure, so as to divide the oven cavity into a first space defining the thermal zone and a second space that is constituted by the remainder of the oven cavity and which is set apart from the thermal zone. The insert includes a body and a working surface on the body which faces the thermal zone.

In one preferred embodiment of the assembly, the oven cavity insert is removably mounted on the interior of the door and is configured so as to project into, and thus occupy, an unused portion of the thermal zone when the door is closed.

In another preferred embodiment, an oven cavity insert is removably mounted between two or more opposing interior walls of the enclosure, so as to constitute a transverse wall.

In another preferred embodiment, the oven cavity insert includes at least two oven cavity insert subsections, wherein a plurality of subsections may be assembled to provide the oven insert.

In another preferred embodiment, the oven cavity insert includes an extension means and at least one oven cavity insert subsection mounted on the extension means, whereby the oven cavity insert subsection may be positioned in a first selectable position adjacent a first separation column when the first separation column is mounted in the oven cavity. Movement of the subsection via the extension means allows the insert subsection to be retracted from the first selectable position to a second selectable position to accommodate an additional, e.g., second, separation column mounted in the oven cavity. Movement of the subsection via the extension means allows the insert subsection to be returned from the second selectable position to the first selectable position after the additional separation column is removed from the oven cavity.

In another preferred embodiment, a computer is provided for determining one of a plurality of oven operating conditions, and, in response to a determination of an operating condition, controlling the operation of said temperature control assembly. The plurality of operating conditions includes an inactive oven condition, wherein the computer operates the temperature control assembly to allow a cavity insert or cavity insert subsection(s) to be inserted, exchanged, repaired, removed, etc. in a safe and expeditious manner during the inactive oven condition.

Use of the oven cavity insert allows significant reduction in the cavity volume of prior art chromatographic systems, yet the tasks of accessing the oven cavity and mounting or replacing a conventional separation column located therein are met with ease. The thermal zone, being smaller, may be heated more efficiently and thus the oven consumes less operating power.

BRIEF DESCRIPTION OF THE DRAWINGS

The present invention will be better understood, and its numerous objects and advantages will become apparent by reference to the following detailed description of the invention when taken in conjunction with the following drawings, in which.

DETAILED DESCRIPTION OF THE PREFERRED EMBODIMENT

In one aspect of the present invention, the apparatus and methods of the present invention are directed to the provision of selective temperature control of a component situated in a temperature-controlled thermal zone in an analytical instrument. However the teachings of the present invention may also be applied to any analytical instrument that may benefit from the provision of a controlled temperature in a closed cavity.

The present invention is contemplated for use in a compact and efficient analytical instrument that will find advantageous use not only in a laboratory but also outside of the laboratory. The teachings of the present invention may therefore be applied to both portable and laboratory-based analytical instruments, as well as to other types of portable instruments that may benefit from the provision of a temperature controlled thermal zone or a selectable cavity volume.

"Thermal zone" is meant to describe a temperature-controlled volume of air within which a component is positioned and, thereby, subject to the air temperature in the thermal zone. In effect, the function of the thermal zone is to control the temperature of the component by way of a temperature-controlled air bath.

"Component" is meant to include one or more devices, subsystems, or apparatus that may form a portion of an analytical instrument. In the illustrated embodiments, a separation column may be mounted as a component in an oven in a gas chromatograph. However, the invention contemplates the use of the present invention for temperature control of other components as well.

"Analysis" and "analytical" are meant broadly to include both qualitative and quantitative analytical methods, detection, or observation of physical or chemical parameters. For example, the apparatus and methods described herein may be applied to directly or indirectly effect selective temperature control of an element, substance, or material in the form of a "sample" that is present in, or processed by, such analysis.

"Chromatographic" analysis of a sample is the preferred mode of analysis according to the practice of the present invention, and the following description of the invention will be directed to an analytical instrument in the form of a compact gas chromatographic analytical system (hereinafter, a chromatography). However, the teachings herein may be applied to analytical instruments for effecting a chromatographic analysis of liquids, multiple component gases and liquids, and mixtures thereof capable of flow. Moreover, it should be understood that the teachings herein are applicable to instruments that operate using other instrument methods or that analyze or detect other physical parameters and phenomena. Sample extraction or sample trapping are but two such methods that represent alternative applications.

Figure 3A:
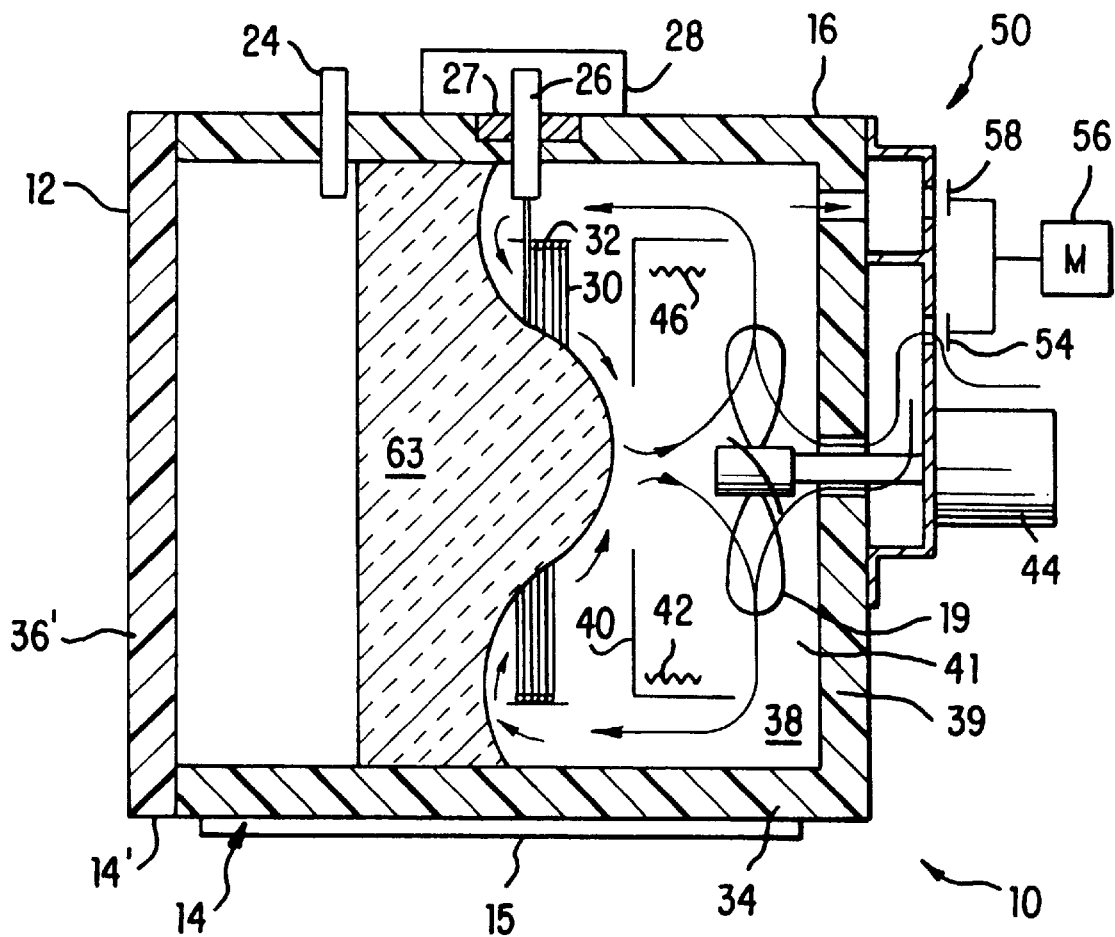
FIG. 3A is a side sectional view of a third preferred embodiment of the chromatograph of FIG. 1 during an active operating condition, wherein a single separation column is installed in the oven cavity.
Figure 3B:
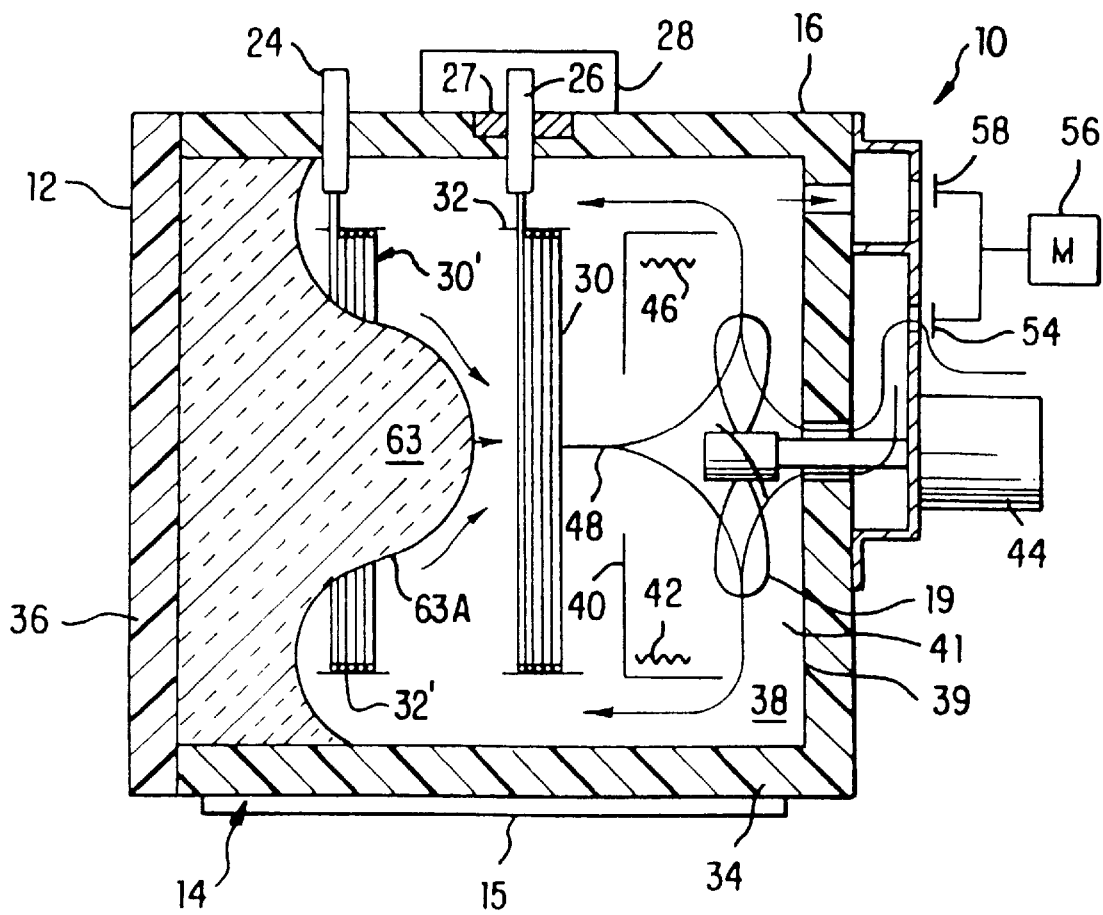
FIG. 3B is a side sectional view of a third preferred embodiment of the chromatograph of FIG. 2A during an active operating condition, wherein a plurality of separation columns are installed in the oven cavity.
Figure 4A:
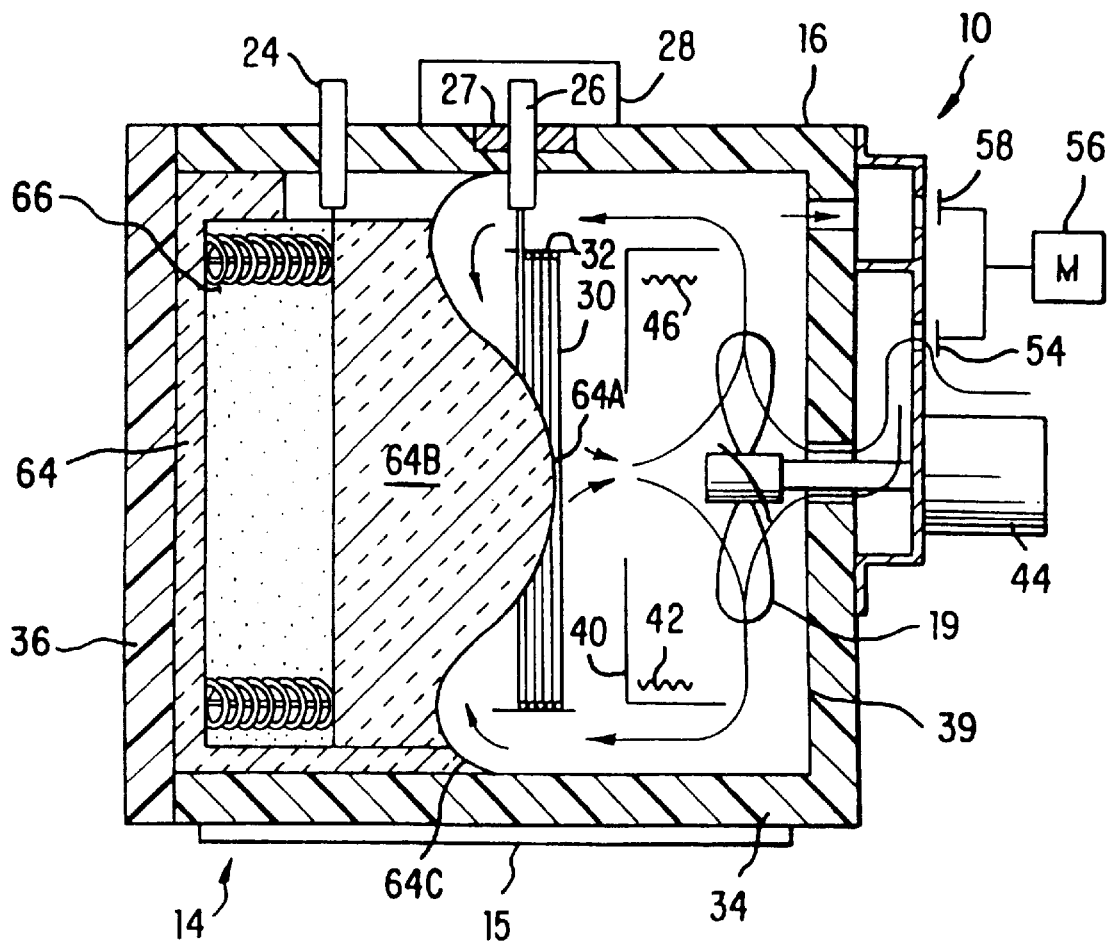
FIG. 4A is a side sectional view of a fourth preferred embodiment of the chromatograph of FIG. 1 during an active operating condition, wherein a single separation column is installed in the oven cavity.
Figure 4B:
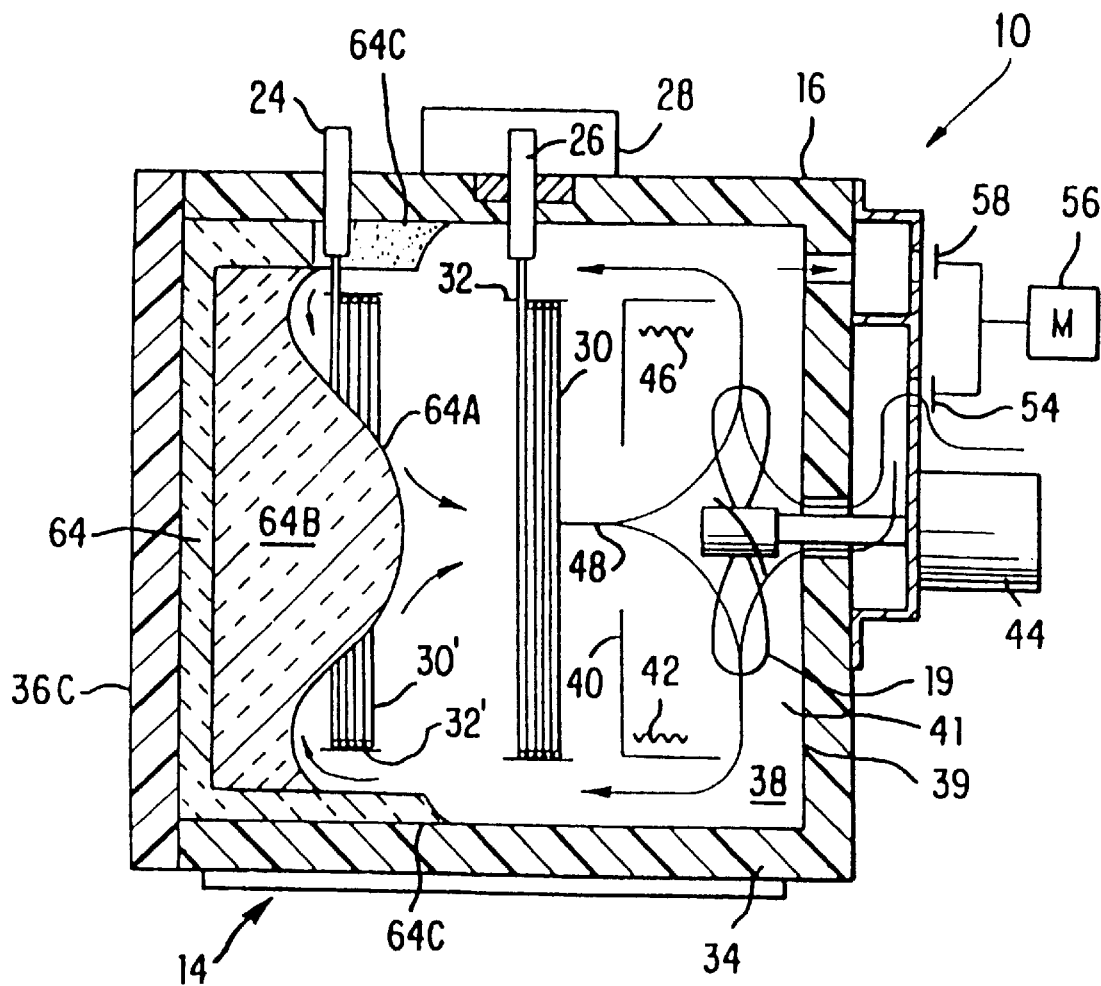
FIG. 4B is a side sectional view of the fourth preferred embodiment in FIG. 3A during an active operating condition, wherein a plurality of separation columns are installed in the oven cavity.
Figure 5:
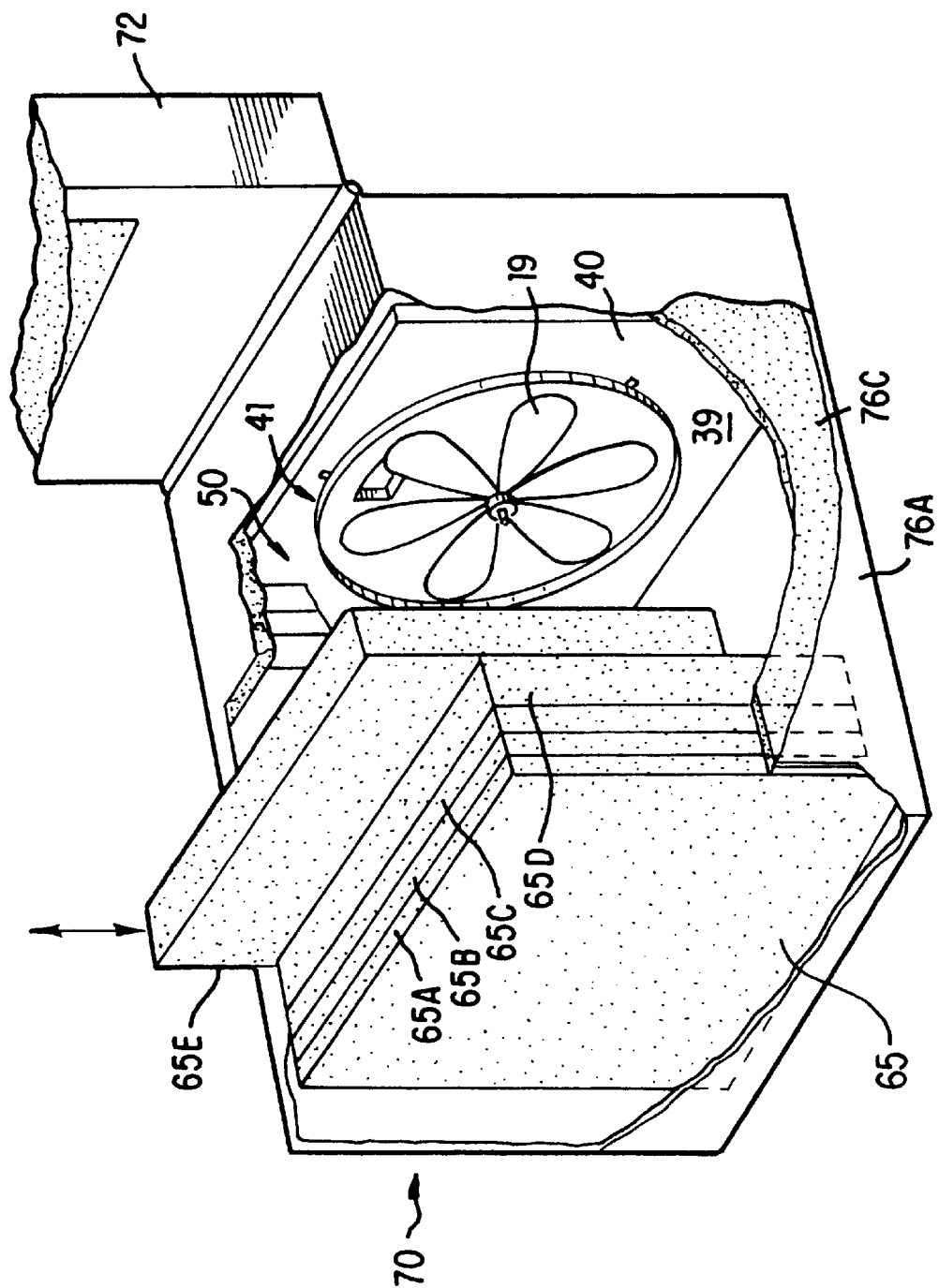
FIG. 5 is a side perspective view of a fifth preferred embodiment of an oven insert located in a top-loading version of chromatograph of FIG. 1, with a partial cutaway view of the oven cavity, during an inactive operating condition, wherein a plurality of insulating insert subsections are being installed in the oven cavity.

A first preferred embodiment of a new and novel gas chromatograph are shown in FIGS. 1A–1B and 3A–4B and is generally designated 10; a second preferred embodiment of a new and novel gas chromatograph is shown in FIG. 5 and is generally designated 70. In the illustrated embodiment, the gas chromatographs 10, 70 may be versions of a Hewlett-Packard 6890 Series Gas Chromatograph that are modified according to the teachings in to include a novel oven cavity insert.

Preferred embodiments of the oven cavity insert are illustrated as follows: in FIG. 1B as insert 61; in FIG. 2A as insert 62; in FIG. 2B as insert 63; in FIGS. 3A–3B as insert 63; in FIGS. 4A–4B as insert 64 having subsection 64B; and in FIG. 5 as insert 65 which includes a combination of oven cavity insert subsections 65A–65D.

As shown in FIGS. 1A–3B, the chromatograph 10 is arranged to perform a chromatographic separation of a given sample compound in an analysis. The illustrated embodiment utilizes a sample injection with a pressurized carrier gas by means of an injection port 24. The carrier gas supplied to injection port 24 is provided from a source through an appropriate valve (not shown), which serves to control the pressure of the carrier gas flowing in a column 30 connected to the injection port 24. However, for the purposes of this description, the sample may be considered as being injected using any conventional technique. A separation column 30 is positioned within an oven housing 16 having an oven cavity 38, a heating unit 18, and a temperature sensor 32. A temperature control assembly 18 provides heat or cooling to a thermal zone in the oven cavity 38 in response to a control signal generated by computer 22, as known in the art. In order to ensure that the temperature within the oven housing 16 is at a desired level, sensor 32 generates a feedback signal representative of the temperature in oven cavity 38, which signal is provided to computer 22. The carrier gas/sample combination passing through column 30 is exposed to a temperature profile resulting in part from the operation of the temperature control assembly 18 within the oven 16. During this profile of changing temperatures, i.e., rising or falling, the sample will separate into its components primarily due to differences in the volatility characteristics of each component at a given temperature. As the components exit column 30 they are detected by detector 28 having a fitting 26.

Oven housing 16 has a cubic shaped cavity 38 formed by an insulated enclosure 34 having exterior shell 36, top wall 36D, bottom wall 36E, rear wall 39, and side walls 36A, 36B as viewed from the front. The particular embodiment of the oven housing 16 includes door opening facing strips 14, 14' behind which are compartments in the enclosure 34 that are filled with insulation 36C. An insulated door 12 is mounted on enclosure 34 and is movable between an open position (illustrated in FIG. 1B, which provides access to the oven cavity 38) and a closed position (illustrated in FIG. 1A, which completely closes off and contains oven cavity 38).

The temperature control assembly 18 includes an oven vent assembly 50 and an oven fan assembly 41 that can be located at any interior wall of the enclosure 34, but as shown they are located opposite the oven door 12 and thus at the rear wall 39. The oven vent assembly 50 includes intake and exhaust ports, preferably, provided as airways that extend through the rear wall 39. The intake and exhaust ports may be selectably opened or closed by positioning of flaps 54, 58 by motor 56 in the oven vent assembly 50. It is contemplated that the oven door 12 is hinged to allow access to the oven cavity 38. When the intake and exhaust ports are covered, and when the door 12 is closed, the oven 16 defines a substantially closed, thermally-insulated cavity volume of air which, for convenience, will be termed the cavity air.

Mounted in the oven cavity 38 behind the space containing the column 30 is a transverse baffle 40 of sheet metal having a central opening covered by a protective grid. Baffle 40 is square shaped and is connected at its four corners to the interior side walls 36A, 36B of enclosure 34. The dimensions of baffle 40 are less than that of the corresponding dimensions of cavity 38 to provide a peripheral space permitting air to flow from the rear of the oven compartment towards the front as shown by arrows. A fan 19 is mounted behind baffle 40 and is surrounded by an oven heater 42,46. Fan 19 is driven by motor 44. The oven fan 19 is mounted on a shaft extending through the rear wall 39 and is rotatable by known techniques in a selected direction. The fan 19 circulates air within the oven cavity 38 so as to provide a thermal zone as will now be described.

The baffle 40 in the oven defines a circular central opening about the oven fan 19. The oven heaters 42, 46 are mounted on the baffle 40 in a plane parallel to the rear wall 39 and the door 12 at a point just forward of the fan 19. The baffle 40 is spaced from the inner side walls by tabs so as to provide a structure having a matrix of openings through which cavity airflow may occur in a stirring flow. As indicated by arrows that represent air flow direction, cavity air is normally taken from the front of the baffle through the central opening and is thrown outwardly by the fan 42, across heaters 42, 46 and then forwardly into the front portion of cavity 38. Thus, the stirring flow of air in the oven cavity is preferably effected in the form of a vortex 48. The baffle 40 creates turbulence and provides air mixing to insure a uniform temperature within the thermal zone. The oven fan 19 may also be rotated in a direction by motor 44 so as to move cavity air through the exhaust port and the intake port may be used to allow ambient air to enter the cavity 38. The opening and closing of flaps 54 and 58 along with regulation of the heater 46 are used to regulate the desired temperature within the oven 16. Heaters 42, 46 are illustrated as resistive heating units, or may be provided in the form of a thermoelectric heating and cooling device such as a Peltier device, or as a combined heating and cryogenic cooling device.

Computer 22 maintains overall control of a plurality of functions associated with the operation of the gas chromatograph 10. The computer 22 provides coordinated control of temperature control assembly 18, the oven vent assembly 50, and the oven fan assembly 41. Sensor 32 senses the temperature in oven 16 and transmits a feedback signal representative of such temperature to computer 22. Computer 22 may, thereby, regulate the flow of ambient air into the oven cavity 38, and the flow of cavity air about the oven heater 42, 46 to establish the desired temperature in the oven cavity 38. Although computer 22 is shown as a single block, such computer, preferably, includes one or more printed circuit board assemblies and includes a central processing unit and all associated peripheral devices, such as random access memories, read-only memories, input/output isolation devices, clocks, drivers, power supply, interface circuits, and other related electronic components. As such, computer 22 includes a memory in which information and programming, directed to a plurality of control functions can be stored and retrieved by known methods. Accordingly, the chromatograph 10 includes a control panel 25 connected to computer 22. The control panel 25 includes data entry devices such as keypad 25A for entry of various pieces of information into computer 22 by the user, and computer 22 operates to act upon the entered information or to store the entered information into memory for later access. Control panel 25 is provided with a display screen 25D. Consequently, indicating or prompt messages, such as may be pertinent to a shutdown or an inactive mode, can be generated by computer 22 and displayed on the display screen 25D. In particular, such information, programming, and control functions are contemplated as being directed to safe operation of the chromatograph 10 during at least one inactive operating condition, wherein the oven housing 16 is subject to removal or insertion of a cavity insert. By monitoring the operating conditions in the gas chromatograph 10, and issuing commands to the oven vent assembly 50 and the oven fan assembly 41, the computer 22 can provide an appropriate mode, whereby oven inactivity allows for safe and expeditious removal or reinsertion of the insert 61, or of the column 30, or other components located in the oven cavity 38. The preferred embodiment of the chromatograph 10 in FIGS. 1–4 is illustrated as a front-loading chromatograph, and in FIG. 5 illustrated as a top-loading configuration 70, although the description herein is generally applicable to both embodiments.

In a particular feature of the invention, those skilled in the art will recognize that any unused space within the thermal zone in the oven cavity 38 wastes energy; further, as the volume of the oven cavity is reduced, less power is required to heat or cool the oven cavity and the efficiency of the temperature control assembly 18 is increased. Furthermore, as the volume of the oven cavity is reduced, the thermal mass presented by the oven housing 34 to the temperature control assembly 18 can be reduced as well.

Figure 1A:
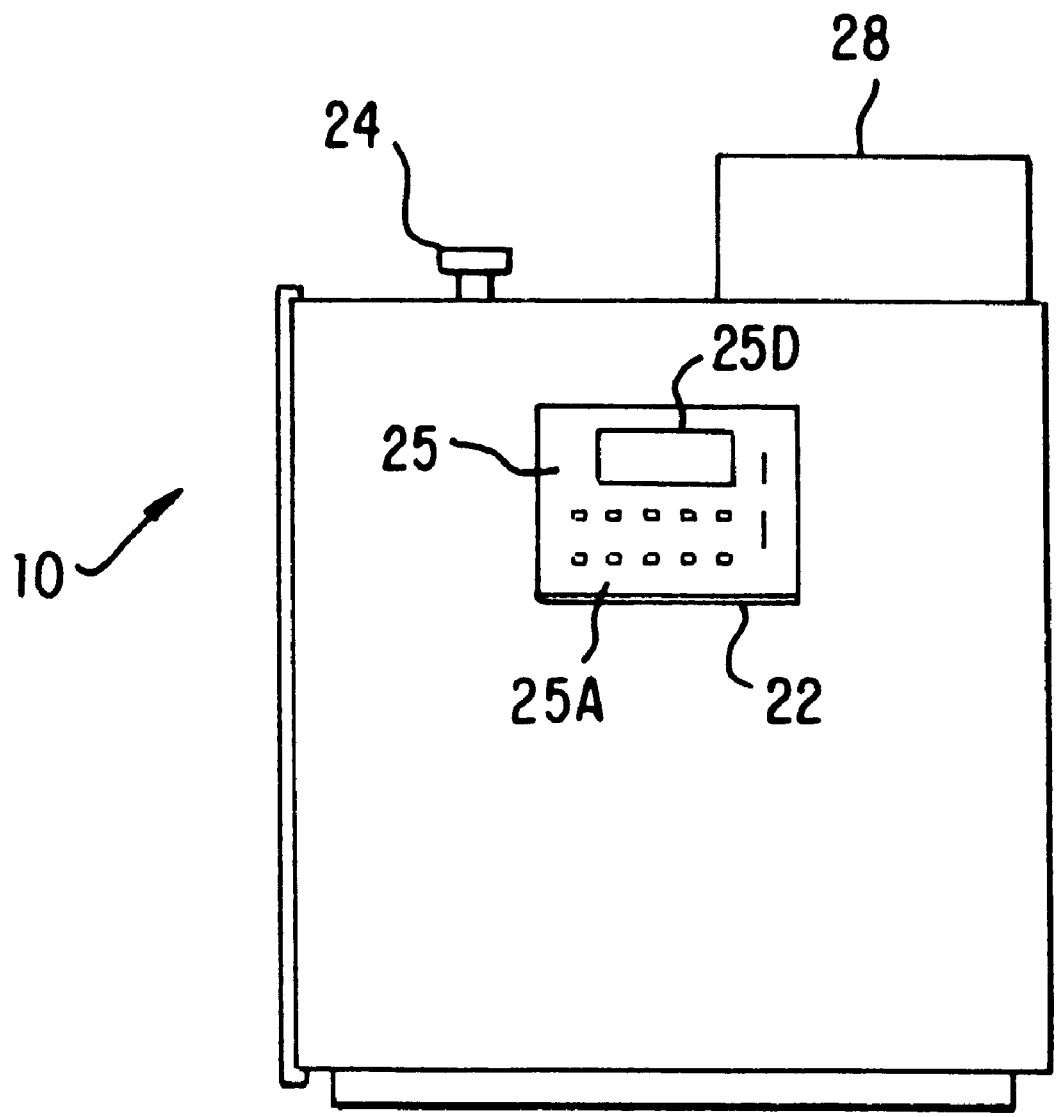
FIGS. 1A and 1B are front perspective views of a novel analytical instrument configured as a chromatograph and constructed in accordance with the present invention.
Figure 1B:
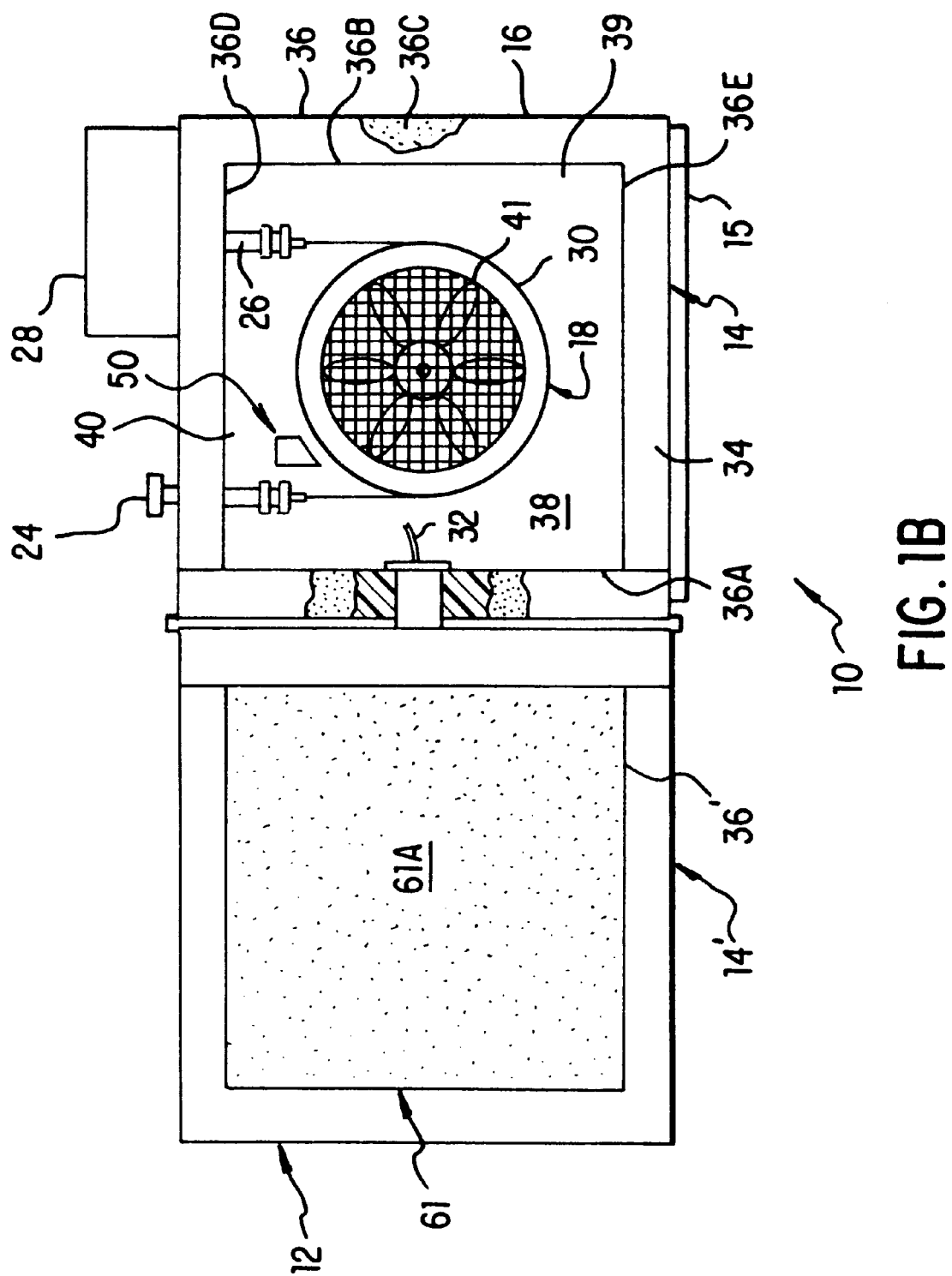

Accordingly, and as shown in FIG. 1B, a first preferred embodiment of an oven cavity insert 61 is removably located on the inwardly-facing side of the insulated portion of the oven cavity door 12, so as to provide a working surface 61A that projects into the oven cavity 38 to an extent sufficient to occupy at least a portion of the unused space in the cavity 38. Preferably, the insert 61 is shaped to occupy as much of the unused space in the oven cavity 38 as possible without obstructing the circulation of air in the air bath described above with respect to the column 30. Insert 61, like the insulation in the enclosure 34, is constructed, preferably, of material that impedes heat transfer between the thermal zone and ambient conditions. Commonly-known, high-temperature (e.g., refractory) insulating materials are suitable. A protective "skin" of heat-resistant or heat-reflecting material as known in the art, such as a mesh of glass fiber or metallic strands, may be incorporated in the working surface 61A so as to impede heat transfer in addition to protecting the insert 61 from the effects of handling or impact on the working surface 61A.

Figure 2A:
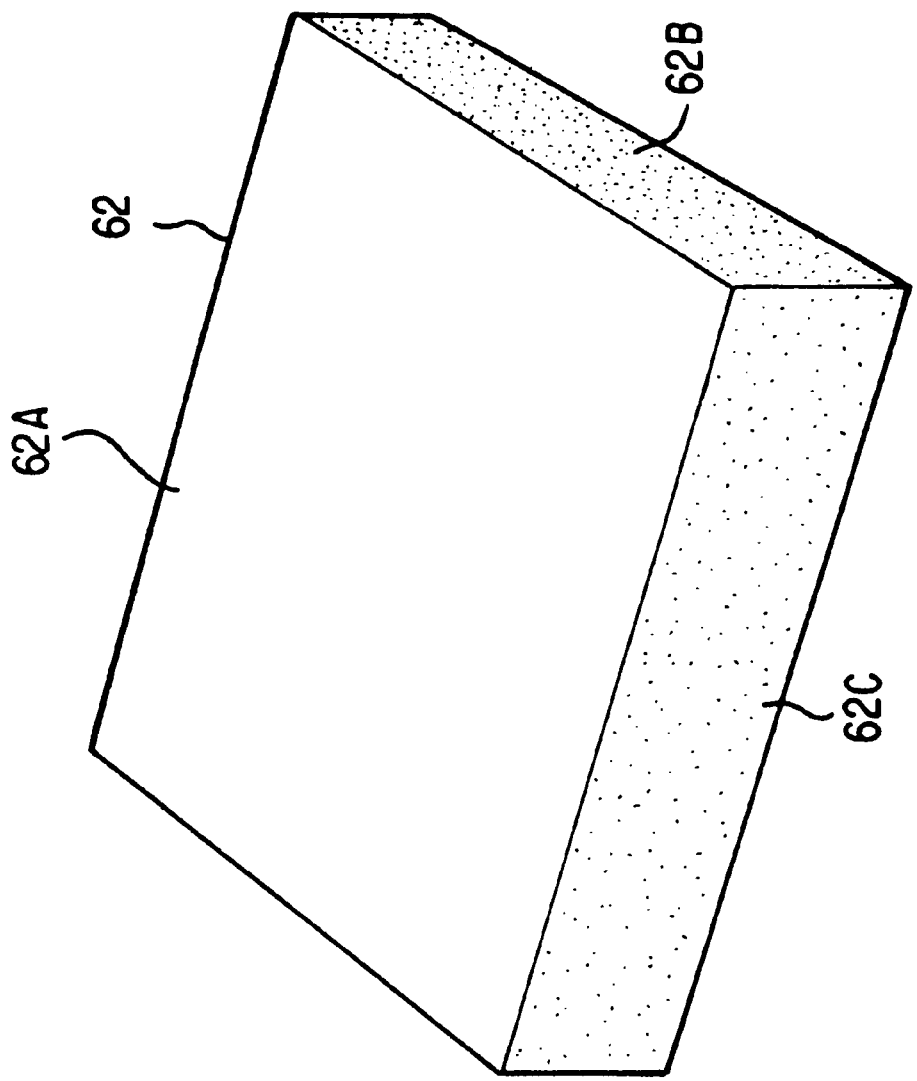
FIGS. 2A and 2B are side perspective views of first and second preferred embodiments of an oven cavity insert constructed in accordance with the present invention and operable in the chromatograph of FIGS. 1A and 1B.
Figure 2B:
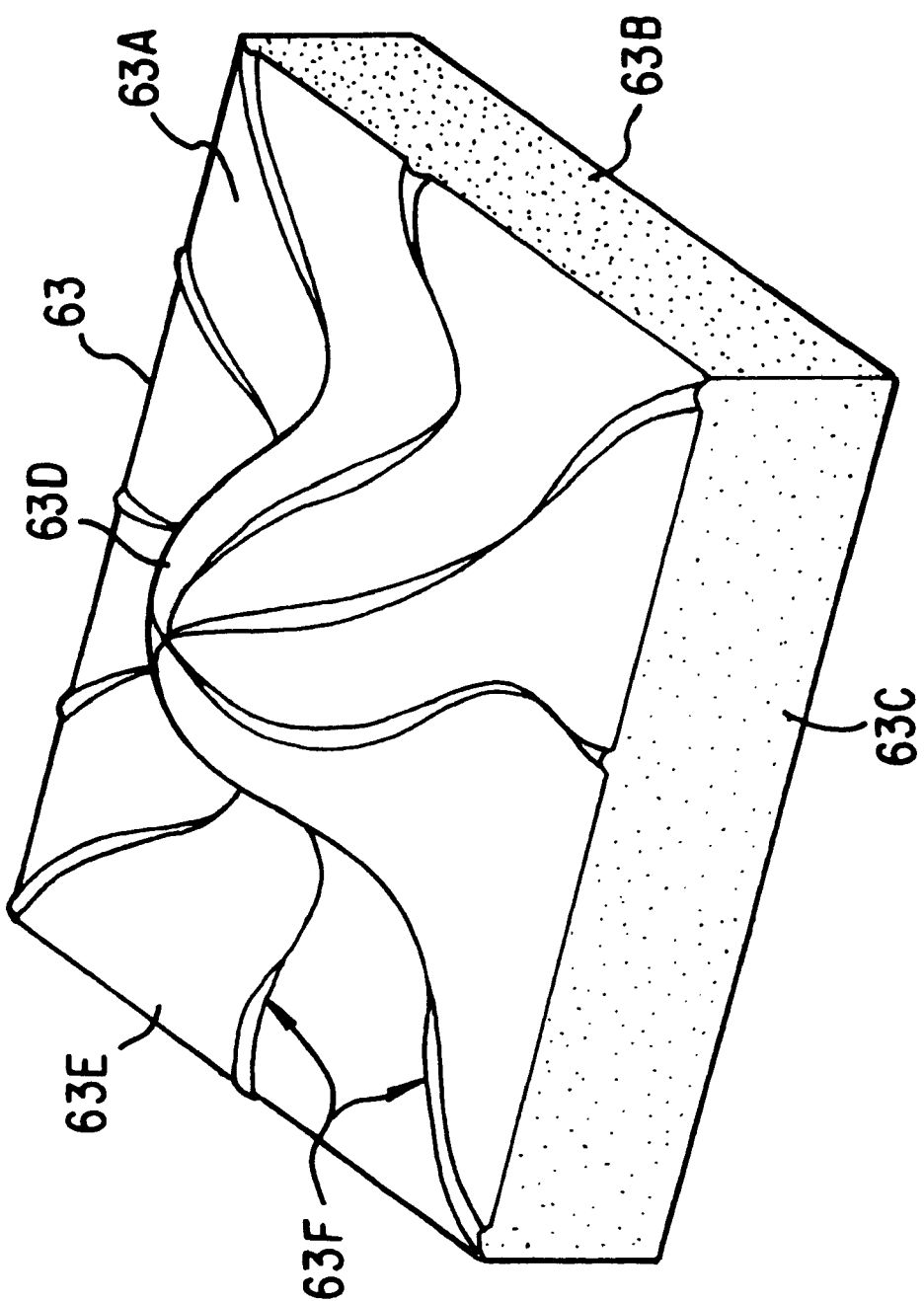

Second and third preferred embodiments 62, 63 of an oven cavity insert are illustrated in FIGS. 2A–2B. As shown in FIG. 2A, the insert 62 is configured as a movable block of insulation which may be inserted by the operator through the door opening of the housing 34 and then positioned transversely to the side walls 36A, 36B, 36D, 36E and within the oven cavity 38 such that the sides 62B, 62C fit snugly against the housing 34. As shown in FIG. 2B, the insert 63 having sides 63B, 63C is also configured as a movable block of insulation which may be inserted by the operator to fit within the housing 34 in a similar fashion. Inserts 62 and 63 include respective working surfaces 62A, 63A which are positioned opposite the column 32. The working surface 63A of insert 63 includes an ellipsoidal protrusion 63D and optional surface features such as shallow spiral fins 63F which promote efficient air flow between the peripheral and the central portions of the oven cavity 38. To avoid the creation of eddy currents in the air bath, the insert 63 includes flared edges 63E to allow a smooth transition between the boundary of the working surface 63A and the oven housing 34 without abrupt discontinuities.

FIGS. 4A and 4B illustrate a fourth preferred embodiment 64 of the oven cavity insert which is similar in shape to insert 63 and includes extension means 66 and a movable insert subsection 64B. To avoid the creation of eddy currents in the air bath, the insert 64 and subsection 64B allow a smooth transition of the working surface 64A at flared edges 64C to the oven housing 34 without abrupt discontinuities.

FIG. 5 illustrates a fifth preferred embodiment 65 of oven cavity insert having oven cavity insert subsections 65A–65E that may be assembled or inserted as necessary to constitute a complete oven cavity insert that occupies a selectable amount of the oven cavity 38. The insert 65 constitutes either: a) an aggregation of oven cavity insert subsections, of which the number, size, and shape may be selected and assembled to create a desired profile in the working surface, or to best fit the enclosure, or to conform to irregularities in the component located in the first space, or in the interior walls of the enclosure; or b) a single oven cavity insert subsection having a predetermined size and shape designed to fit the enclosure In summary, each of the embodiments 61–65 of the oven cavity insert generally include a body having a working surface and formed, preferably, of insulating material, such that the body is positionable in the oven cavity so as to divide the oven cavity into a first space and a second space, wherein a component such as the column 30 (and optionally the additional column 30') may be located opposite the working surface and be fully functional in the first space, and wherein heat transfer is impeded between the first space and the second space by the oven cavity insert. Hence, and depending upon the application, the body, or the working surface, or both, may be formed of a known material or construction so as to impede heat transfer between the first space and the second space; further, any of the embodiments of the oven cavity insert may optionally include a working surface formed of heat-reflecting material so as to further impede heat transfer between the first space to the second space.

As particularly illustrated in FIGS. 2B and 3A–4B, the working surface of the oven cavity insert is shaped so as to allow a marginal amount of cavity volume disposed about the column 30 so as to permit efficient circulation 48 of air around the component for efficient temperature control of the component.

While the invention has been described and illustrated with reference to specific embodiments, those skilled in the art will recognize that modification and variations may be made without departing from the principles of the invention as described herein above and set forth in the following claims.

What is claimed is:

1. An oven cavity insert for use in temperature control of a component situated in an oven cavity defined by an enclosure in an analytical instrument, comprising:
   a body positionable within the oven cavity, wherein the body exhibits a size and shape sufficient to fit transversely within the enclosure so as to divide the oven cavity into a first space defining a thermal zone and a second space that is constituted by the remainder of the oven cavity and which is set apart from the thermal zone, wherein the component is located in the thermal zone and the body includes a working surface which faces the thermal zone, wherein the working surface of the oven cavity insert is shaped so as to conform to a thermal envelope about the component, whereby the thermal envelope corresponds to the volume occupied by the component located in the thermal zone and includes a marginal volume disposed about the component so as to permit air flow around the component for efficient temperature control of the component, and wherein the oven cavity insert is constructed to impede heat transfer between the first and second spaces.

2. The oven cavity insert of claim 1, wherein the working surface further comprises an insulating material so as to impede heat transfer between the first space and the second space.

3. The oven cavity insert of claim 1, wherein the working surface further comprises a heat-reflecting material so as to impede heat transfer between the first space and the second space.

4. The oven cavity insert of claim 1, wherein the body further comprises an insulating material so as to impede heat transfer between the first space and the second space.

5. A chromatographic assembly, comprising:
   a housing having an insulating enclosure for confining an oven cavity defined therein, a temperature control assembly for establishing a thermal zone in the oven cavity, an injector section, a detector section, and a separation column located within temperature-controlled zone and having inlet and outlet ends attached to the injector section and detector section, wherein the housing includes a door mounted on a door opening in the enclosure which allows access to the temperature-controlled zone, and an oven cavity insert positionable within the oven cavity, wherein the insert includes a body and a working surface on the body which faces the thermal zone, and wherein the body exhibits a size and shape sufficient to fit transversely within the enclosure so as to divide the oven cavity into a first space defining the thermal zone and a second space that is constituted by the remainder of the oven cavity and which is set apart from the thermal zone.

6. The assembly of claim 5, wherein the oven cavity insert is removably mounted on the interior of the door and is configured so as to project into, and thus occupy, an unused portion of the thermal zone when the door is closed.

7. The assembly of claim 5, wherein the oven cavity insert is removably mounted between two or more opposing interior walls of the enclosure, so as to constitute a transverse wall.

8. The assembly of claim 5, wherein the oven cavity insert includes at least two oven cavity insert subsections, whereby a plurality of subsections may be assembled to provide the oven insert.

9. The assembly of claim 5, wherein the oven cavity insert includes an extension means and at least one oven cavity insert subsection mounted on the extension means, whereby the oven cavity insert subsection may be positioned in a first selectable position adjacent a first separation column when the first separation column is mounted in the oven cavity, and wherein movement of the subsection via the extension means allows the insert subsection to be retracted from the first selectable position to a second selectable position to accommodate an additional separation column mounted in the oven cavity.

10. The assembly of claim 5, further comprising a computer for determining one of a plurality of oven operating conditions, and, in response to a determination of an operating condition, controlling the operation of said temperature control assembly, and wherein the plurality of operating conditions includes an inactive oven condition, wherein the computer operates the temperature control assembly to allow the cavity insert to be located with respect to the oven cavity during the inactive oven condition.

11. An oven cavity insert for use in temperature control of a component situated in an oven cavity defined by an enclosure in an analytical instrument, comprising:
   a body positionable within the oven cavity, wherein the body exhibits a size and shape sufficient to fit transversely within the enclosure so as to divide the oven cavity into a first space defining a thermal zone and a second space that is constituted by the remainder of the oven cavity and which is set apart from the thermal zone, wherein the component is located in the thermal zone and the body includes a working surface which faces the thermal zone, wherein the component is provided in the form of a separation column located in a central portion of the first space, and wherein the working surface of the oven cavity insert is shaped to include a central protrusion which extends into the central portion of the first space, whereby air flow about the separation column is circulated between the perimeter of the first space and the central portion of the first space, and wherein the oven cavity insert is constructed to impede heat transfer between the first and second spaces.

12. The oven cavity insert of claim 11, wherein the working surface further comprises an insulating material so as to impede heat transfer between the first space and the second space.

13. The oven cavity insert of claim 11, wherein the working surface further comprises a heat-reflecting material so as to impede heat transfer between the first space and the second space.

14. The oven cavity insert of claim 11, wherein the body further comprises an insulating material so as to impede heat transfer between the first space and the second space.

15. An oven cavity insert for use in temperature control of a component situated in an oven cavity defined by an enclosure in an analytical instrument, comprising:

a body positionable within the oven cavity, wherein the body exhibits a size and shape sufficient to fit transversely within the enclosure so as to divide the oven cavity into a first space defining a thermal zone and a second space that is constituted by the remainder of the oven cavity and which is set apart from the thermal zone, wherein the component is located in the thermal zone and the body includes a working surface which faces the thermal zone, wherein the working surface of the oven cavity insert is shaped to include a surface feature wherein air flow about the component is directed to flow between the perimeter of the first space and the central portion of the first space, and whereby efficient circulation of air flow through the thermal zone is effected and eddy currents in the air flow are avoided, and wherein the oven cavity insert is constructed to impede heat transfer between the first and second spaces.

16. The oven cavity insert of claim 15, wherein the working surface further comprises an insulating material so as to impede heat transfer between the first space and the second space.

17. The oven cavity insert of claim 15, wherein the working surface further comprises a heat-reflecting material so as to impede heat transfer between the first space and the second space.

18. The oven cavity insert of claim 15, wherein the body further comprises an insulating material so as to impede heat transfer between the first space and the second space.

19. An oven cavity insert for use in temperature control of a component situated in an oven cavity defined by an enclosure in an analytical instrument, comprising:

a body positionable within the oven cavity, wherein the body exhibits a size and shape sufficient to fit transversely within the enclosure so as to divide the oven cavity into a first space defining a thermal zone and a second space that is constituted by the remainder of the oven cavity and which is set apart from the thermal zone, wherein the component is located in the thermal zone and the body includes a working surface which faces the thermal zone, wherein the working surface includes a surface feature configured to promote a vortex pattern of air flow over the working surface, and wherein the oven cavity insert is constructed to impede heat transfer between the first and second spaces.

20. The oven cavity insert of claim 19, wherein the working surface further comprises an insulating material so as to impede heat transfer between the first space and the second space.

21. The oven cavity insert of claim 19, wherein the working surface further comprises a heat-reflecting material so as to impede heat transfer between the first space and the second space.

22. The oven cavity insert of claim 19, wherein the body further comprises an insulating material so as to impede heat transfer between the first space and the second space.

23. An oven cavity insert for use in temperature control of a component situated in an oven cavity defined by an enclosure in an analytical instrument, comprising:

a body positionable within the oven cavity, wherein the body exhibits a size and shape sufficient to fit transversely within the enclosure so as to divide the oven cavity into a first space defining a thermal zone and a second space that is constituted by the remainder of the oven cavity and which is set apart from the thermal zone, wherein the component is located in the thermal zone and the body includes a working surface which faces the thermal zone, wherein the working surface includes a flared outer edge configured to merge with the enclosure, wherein efficient circulation of air flow through the thermal zone is effected and eddy currents in the air flow are minimized, and wherein the oven cavity insert is constructed to impede heat transfer between the first and second spaces.

24. The oven cavity insert of claim 23, wherein the working surface further comprises an insulating material so as to impede heat transfer between the first space and the second space.

25. The oven cavity insert of claim 23, wherein the working surface further comprises a heat-reflecting material so as to impede heat transfer between the first space and the second space.

26. The oven cavity insert of claim 23, wherein the body further comprises an insulating material so as to impede heat transfer between the first space and the second space.

* * * * *